US010268924B2

United States Patent
Gu et al.

(10) Patent No.: US 10,268,924 B2
(45) Date of Patent: Apr. 23, 2019

(54) SYSTEMS AND METHODS FOR INTEGRATED CARGO INSPECTION

(71) Applicant: SAP SE, Walldorf (DE)

(72) Inventors: Richard Gu, Shanghai (CN); Qiu Liang, Guangdong (CN); Jinming Wang, Shanghai (CN); Natalie Zhang, Guangdong (CN); Benjamin Dong, Shanghai (CN); Alex Huang, Shanghai (CN); James Ao, Guangdong (CN)

(73) Assignee: SAP SE, Walldorf (DE)

(*) Notice: Subject to any disclaimer, the term of this patent is extended or adjusted under 35 U.S.C. 154(b) by 0 days.

(21) Appl. No.: 15/369,085

(22) Filed: Dec. 5, 2016

(65) Prior Publication Data

US 2018/0157932 A1 Jun. 7, 2018

(51) Int. Cl.

| G06K 9/62 | (2006.01) |
|---|---|
| G06N 99/00 | (2019.01) |
| G06K 9/00 | (2006.01) |
| G06N 20/00 | (2019.01) |
| G01N 23/04 | (2018.01) |

(Continued)

(52) U.S. Cl.
CPC ........... *G06K 9/6227* (2013.01); *G01N 23/04* (2013.01); *G06K 9/0063* (2013.01); *G06N 20/00* (2019.01); *G06N 99/005* (2013.01); *G06Q 10/08* (2013.01); *G06Q 50/28* (2013.01); *G01V 5/0008* (2013.01)

(58) Field of Classification Search
CPC ... G06K 9/6227; G06K 9/0063; G06N 99/005
See application file for complete search history.

(56) References Cited

U.S. PATENT DOCUMENTS

| 2014/0294147 A1 | 10/2014 | Chen et al. |
| 2015/0121528 A1* | 4/2015 | Crowley ............. H04L 63/1441 |
| | | 726/23 |

(Continued)

FOREIGN PATENT DOCUMENTS

| EP | 3067823 A1 | 9/2016 |
| WO | 2007056420 A2 | 5/2007 |
| WO | 2015/159045 A1 | 10/2015 |

OTHER PUBLICATIONS

"Extended European Search Report", European Patent Office, dated Apr. 25, 2018, European Application No. 17001931.9, 8 pp.

(Continued)

*Primary Examiner* — Ruiping Li
(74) *Attorney, Agent, or Firm* — Buckley, Maschoff & Talwalkar LLC

(57) ABSTRACT

A system for integrated cargo inspection includes a non-invasive imaging system scanning a cargo container during an offload operation to obtain a digital image of its contents, a server including a control processor to control components of the system. The components including a computer vision system to perform vision system recognition techniques on the digital image and prepare a report having image icons representing the contents, a machine learning system analytically reviewing the report to generate heuristic analysis used to train the vision system, a computing device displaying at least one of a port plan, a scan view, a results list form dialog, and a results history log graphical displays. A method to implement the system and a non-transitory computer-readable medium are also disclosed.

19 Claims, 8 Drawing Sheets

(51) Int. Cl.
 *G06Q 10/08* (2012.01)
 *G06Q 50/28* (2012.01)
 *G01V 5/00* (2006.01)

(56) References Cited

U.S. PATENT DOCUMENTS

2016/0097877 A1* 4/2016 Parikh .................. G06T 7/0004
 378/57
2017/0046852 A1* 2/2017 Gadi ....................... G06K 9/00

OTHER PUBLICATIONS

"Communication pursuant to Article 94(3) EPC: Office Action", European Patent Office, dated Jan. 3, 2019 (Jan. 3, 2019), European Application No. 17001931.9-1222, 8pp.

* cited by examiner

CONNECTED CARGO INSPECTION 05:00:00 MAP VIEW ⬤SCAN VIEW TABLE VIEW FORM VIEW ABOUT

INSTANT VIEW | RESULT OVERVIEW

SCAN RESULT
TOTAL (10)

| CONTAINER NO. | RESULT | WARNING REASON | YARD | ARRIVAL TIME | CONTACT | TELEPHONE | EMAIL |
|---|---|---|---|---|---|---|---|
| 160107188 | ✓ | CLOTHES:SAFE! | A1 | 2016-01-09 20:13:20 | | | |
| 160107189 | ✓ | CLOTHES:SAFE! | A1 | 2016-01-10 08:20:10 | | | |
| 160107190 | ✓ | CLOTHES:SAFE! | A1 | 2016-01-10 09:50:45 | | | |
| 160107191 | ✓ | CLOTHES:SAFE! | A1 | 2016-01-10 12:23:10 | | | |
| 160107192 | ✓ | CLOTHES:SAFE! | A1 | 2016-01-10 15:32:10 | | | |
| 160107193 | ✓ | CLOTHES:SAFE! | A1 | 2016-01-10 15:13:23 | | | |
| 160107186 | − | CLOTHES:QUANTITY MISMATCHED! | B1 | 2016-01-09 14:13:10 | | | |
| 160107187 | − | CLOTHES:QUANTITY MISMATCHED! | B2 | 2016-01-09 15:01:50 | | | |

FIG. 5C

RESULT REPORT
SCAN RESULT (189,937)
SCAN DATE 2015/11/25

| CONTAINER NO. | DECLAR-ATION | ITEMS DECLARED | PREDICT RESULT | RESULT | WARNING REASON | YARD | ARRIVAL TIME | CONTACT PERSON | TELEPHONE | EMAIL | TRACKING RESULT | RESPONSIBLE PERSON |
|---|---|---|---|---|---|---|---|---|---|---|---|---|
| 160107185 | CHECK | FRUIT | CHECK QUANTITY | ! | FRUIT QUANTITY MISMATCHED! | B1 | 2016-01-09 13:23:10 | | | | COMPLETED | |
| 160107186 | CHECK | CLOTHES, FRUIT | CHECK QUANTITY | ! | CLOTHES QUANTITY MISMATCHED! | B1 | 2016-01-09 14:13:10 | | | | PROCESSING | |
| 160107187 | CHECK | CLOTHES | CHECK QUANTITY | ! | CLOTHES SAFE! | B2 | 2016-01-09 15:01:50 | | | | NOT START | |
| 160107188 | CHECK | CLOTHES | SAFE! | ✓ | CLOTHES SAFE! | A1 | 2016-01-09 20:13:20 | | | | COMPLETED | |
| 160107189 | CHECK | CLOTHES | SAFE! | ✓ | CLOTHES SAFE! | A1 | 2016-01-10 08:20:10 | | | | COMPLETED | |
| 160107190 | CHECK | CLOTHES | SAFE! | ✓ | CLOTHES SAFE! | A1 | 2016-01-10 09:50:45 | | | | COMPLETED | |
| 160107191 | CHECK | CLOTHES | SAFE! | ✓ | CLOTHES SAFE! | A1 | 2016-01-10 12:23:10 | | | | COMPLETED | |
| 160107192 | CHECK | CLOTHES | SAFE! | ✓ | CLOTHES SAFE! | A1 | 2016-01-10 12:32:10 | | | | COMPLETED | |
| 160107193 | CHECK | CLOTHES | SAFE! | ✓ | CLOTHES SAFE! | A1 | 2016-01-10 15:13:23 | | | | COMPLETED | |
| 160107195 | CHECK | FRUIT | SAFE! | ! | CLOTHES ITEM MISS DECLARED! | A1 | 2016-01-10 23:39:11 | | | | COMPLETED | |

FIG. 5D

SYSTEMS AND METHODS FOR INTEGRATED CARGO INSPECTION

BACKGROUND

Importation of cargo is important for a nation's economy, along with the welfare and security of its people and facilities. Cargo inspection is one aspect of security where the cargo is inspected for compliance with the nation's standards. The presence of contraband can be established during inspection of a container and its cargo.

The voluminous amount of containers passing into a nation from its ports makes impractical the opening and physical inspection of every container. For example, about only 5% of cargo entering a country gets selected for examination. Conventional sampling approach with on-site checking is insufficient to adequately handle the volume of cargo being imported.

Non-intrusive inspection techniques are available, but these conventional systems do not solve the root problem of still needing on-site, manual inspection of cargo, which is very costly and not very accurate. Conventional systems can utilize a scanning system (e.g., X-ray) that eliminate the need to open each container. These systems do not obviate the need for the manual sampling inspection.

Conventional security apparatus can only display images. The displayed images are dependent on the human manpower to analyze the image for contraband. The recordation of the inspection currently requires individual customs officers to observe and estimate goods. These shortcomings lead to a high cost and waste of human resource.

Accordingly, a need exists for a more accurate cargo inspection apparatus and process through which contraband can more accurately be detected with minimal false alarms.

BRIEF DESCRIPTION OF THE DRAWINGS

FIGS. 5A-5D depict cargo inspection system graphical displays in accordance with embodiments.

DETAILED DESCRIPTION

In accordance with embodiments, integrated cargo inspection systems and methods provide non-invasive scanning equipment integrated into existing port facilities used during container offload operations from a cargo ship. These port facilities can include, for example, a gantry crane. The scanning equipment can include, for example, an X-ray system, a chemical and/or radiation detection system, and/or any other non-invasive scanning equipment. The scanning equipment can scan a container's contents during the ship offload operation so that the scan is completed prior to the container being released from the gantry crane.

In accordance with embodiments, a non-invasive image scanning system can provide a digital image of the scan results electronically to a computer vision system that is linked to machine learning technology. The computer vision system and/or machine learning technology can analyze the cargo digital scan image for recognition of its goods and any contraband captured in the image. The system can be linked to a datastore containing specific information from the container's bill of lading—for example, classification of goods, quantity, nation of origin, source of origin, manufacturer, etc. Embodying systems and methods can provide a fully integrated approach that provides an automated, full sampling coverage solution towards the identification and analysis of cargo being imported into a country. Comparison of the digital scanned image to cargo declarations by embodying systems and methods can ascertain the compliance with import laws, quotas, and duty fees.

Embodying systems and methods provide automated services that integrate information from various portions of the inspection process to provide customs officials with a cohesive, coherent data record of cargo type, quantity, location, source, etc. This information can be obtained by machine vision image analysis in combination with electronic data record analysis.

Implementation of embodying systems and methods can result in point-of-entry (e.g., border crossing, airport, port) cargo inspection for about 100% of the container content without the enormous manpower effort required by conventional approaches. Full coverage inspection can also be used as a basis for a revenue-generating model that charges importers based on the quantity of goods, and/or containers, that are scanned per given time period.

Figure 1:
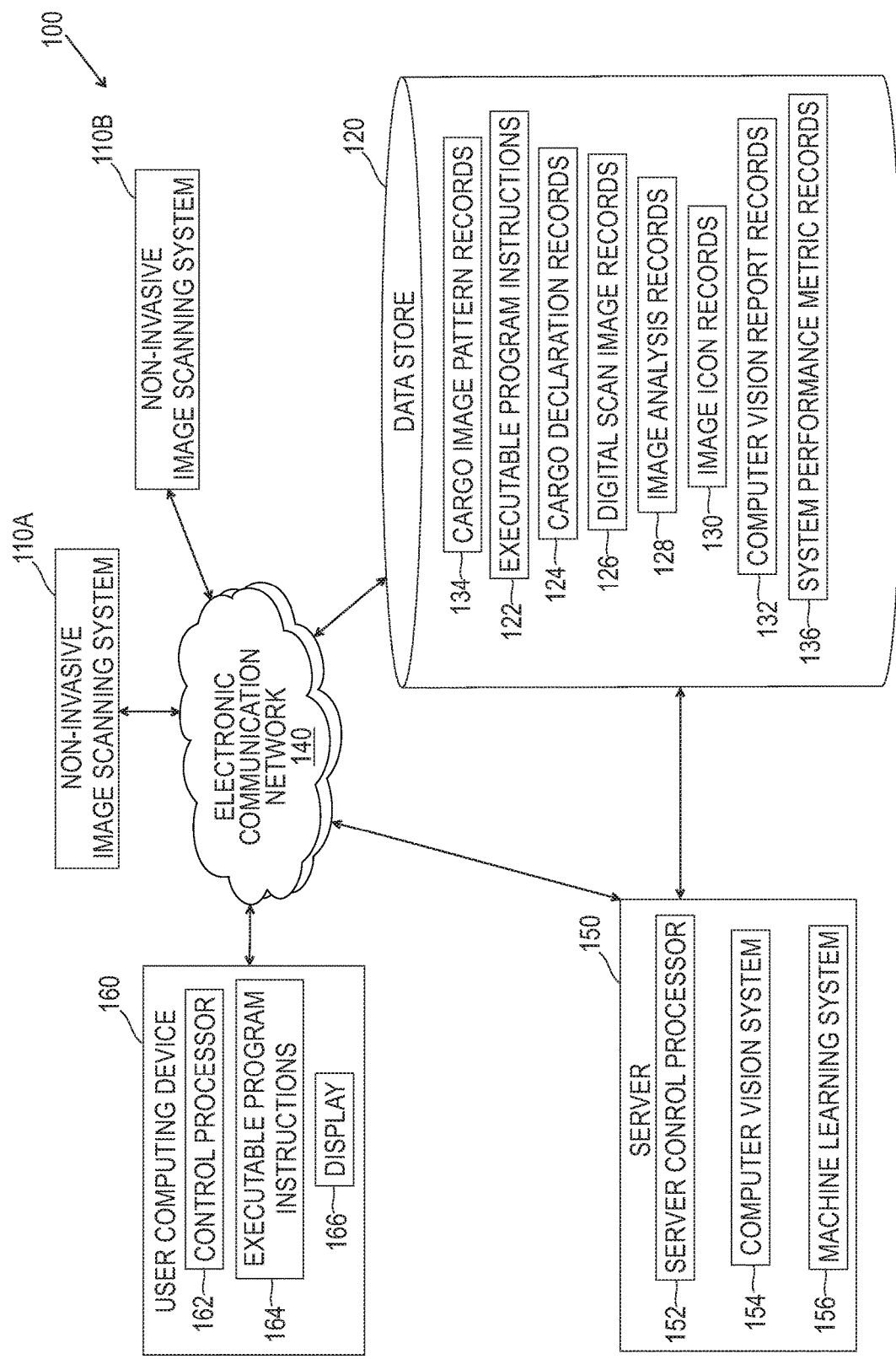
FIG. 1 depicts an integrated cargo inspection system in accordance with embodiments.

FIG. 1 depicts integrated cargo inspection system 100 in accordance with embodiments. An embodying system can include one or more non-invasive image scanning system(s) 110A, 110B (e.g., an x-ray scanning system). In some embodiments, an image scanning system can be a magnetic resonance imaging (MRI) system, a computed tomography imaging system, a positron emission tomography imaging system, or any other imaging system suitable for producing an image of a container's contents by non-invasive scanning of the container.

Each of the non-invasive image scanning systems can be mounted on a gantry crane used to offload shipping containers from cargo ships. In some implementations, the image scanning system(s) 110A, 110B can be mounted in a fixed position, and the container moved in relation to a radiation source of the image scanning system(s) 110A, 110B In other implementations, the image scanning system(s) 110A, 110B can be moveably mounted on the gantry crane, so that the system can move in relation to the container.

Image scanning system 110A, 110B can include an image control processor (not shown) that communicates with other components of the image scanning system (e.g., motor control, memory, radiation source, image gating control, etc.). The image control processor can be in communication with server 150 and data store 120 over electronic communication network 140. Scan images produced by the image scanning system can be stored in digital scan image records 126.

Electronic communication network 140 can be, can comprise, or can be part of, a private internet protocol (IP) network, the Internet, an integrated services digital network (ISDN), frame relay connections, a modem connected to a phone line, a public switched telephone network (PSTN), a public or private data network, a local area network (LAN), a metropolitan area network (MAN), a wide area network (WAN), a wireline or wireless network, a local, regional, or global communication network, an enterprise intranet, any combination of the preceding, and/or any other suitable communication means. It should be recognized that techniques and systems disclosed herein are not limited by the nature of network 140.

Server 150 can include at least one server control processor 152 configured to support embodying operations by executing executable program instructions 122 accessible by the control processor. Dedicated hardware, software modules, and/or firmware can implement embodying services disclosed herein. Server 150 is in communication with data store 120, either directly and/or across electronic communication network 140.

In accordance with embodiments, server 150 can incorporate servlet technology. For example, each stage in unloading the cargo can result in the generation of a JSON format request posting for the server to change the status of cargo and/or container. The server acts on the request by recording status in the data store. The status can be provided for display on display 166 of user computing device 160.

User computing device 160 can be of any type of computing device suitable for use by an end user in performance of the end user's purpose (e.g., personal computer, workstation, thin client, netbook, notebook, tablet computer, mobile device, etc.). User computing device 160 can include client control processor 162 that communicates with other components of the client computing device. Control processor 162 accesses computer executable program instructions 164, which can include an operating system, and software applications. User computing device 160 can be in bidirectional communication with server 150, and other components of system 100, across electronic communication network 140.

The data store 120 can include executable program instructions 122 that can configure server control processor 152 to perform control of modules configured to implement embodying operations. Elements within the data store 120 can be accessed by computer vision system 154. The computer vision system 154 can access digital scan image records 126 to perform vision system recognition techniques on the scanned image. The computer vision system 154 can access an electronic cargo declaration in cargo declaration records 124. The accessed cargo declaration is associated with the container that was the source of the digital image undergoing analysis. In accordance with implementations, this digital image undergoing analysis can be provided from the image scanning system, or the digital scan image records 126.

Cargo identifiers detailed within the cargo declaration can be used by the computer vision system 154 to select cargo image pattern samples stored in cargo image pattern records 134. Computer vision system 154 can compare the digital scan image of the cargo to the image pattern samples to perform its vision system recognition techniques.

In accordance with embodiments, graphical displays (for example, FIGS. 5A-5C) can provide customs officers with information regarding the operational status of system 100, location of containers, container contents, cargo declaration statements (provided to customs officials), and other information. These graphical displays can be displayed on display 166.

Figure 2A:
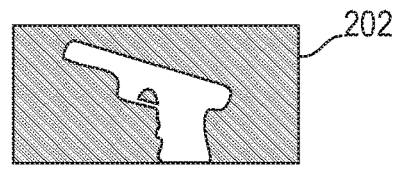
FIGS. 2A-2C depict cargo image pattern samples in accordance with embodiments.
Figure 2B:
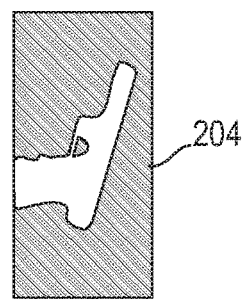
Figure 2C:
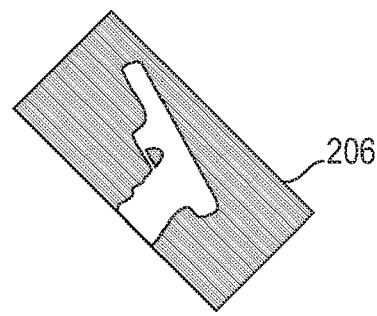

FIGS. 2A-2C depict illustrations of cargo image pattern samples 202, 204, 206 in accordance with embodiments. These cargo image patterns are for one possible type of contraband (i.e., a pistol). Each of FIGS. 2A-2C depict the image pattern at different orientations. It should be readily understood that image patterns of other types of non-contraband and contraband are within the scope of this disclosure. Further, additional orientations of image patterns is also within the scope. In some implementations, the cargo image pattern can be a 3D representation. Computer vision system 154 can access the 3D image, and rotate the image to various orientations when analyzing the cargo digital scan image.

Image icon records 130 can be used by computer vision system 154 to produce a computer vision report that includes image icons representing container contents recognized by the computer vision system. Each of the image icons can depict an outline drawing of a particular type of cargo (e.g., a fruit, an item of clothing, etc.) and/or contraband (e.g., a gun, a knife, etc.). The generated computer vision report can be stored in computer vision report records 132.

Machine learning system 154 can analyze the computer vision report in comparison to the image icon records and/or the digital scan image records. The machine learning system can heuristically improve the analysis performed by computer vision system 154. In accordance with embodiments, a machine learning method (e.g., implemented by a support vector machine) can train a model by accessing cargo image pattern samples stored in cargo image pattern records 134. This model can be used to detect images from computer vision system 154. Training evaluation can include accuracy, detection, and discrimination performance metrics in making a determination of where/how the computer vision system analysis can be improved. System performance metric records 136 can include results of the machine learning system analysis, so that metrics can be analyzed over time to improve recognition by the computer vision system.

In accordance with embodiments, analysis of system performance metrics 136 can achieve better collection, processing and sharing of cargo information. The analysis of performance metrics can result in increased accuracy in computer vision system 154 identification analysis of cargo within the container. Application scenarios for embodying cargo inspection systems and methods can include intelligent terminal management, cargo tracking services, live biometric warning, etc.

Figure 3:
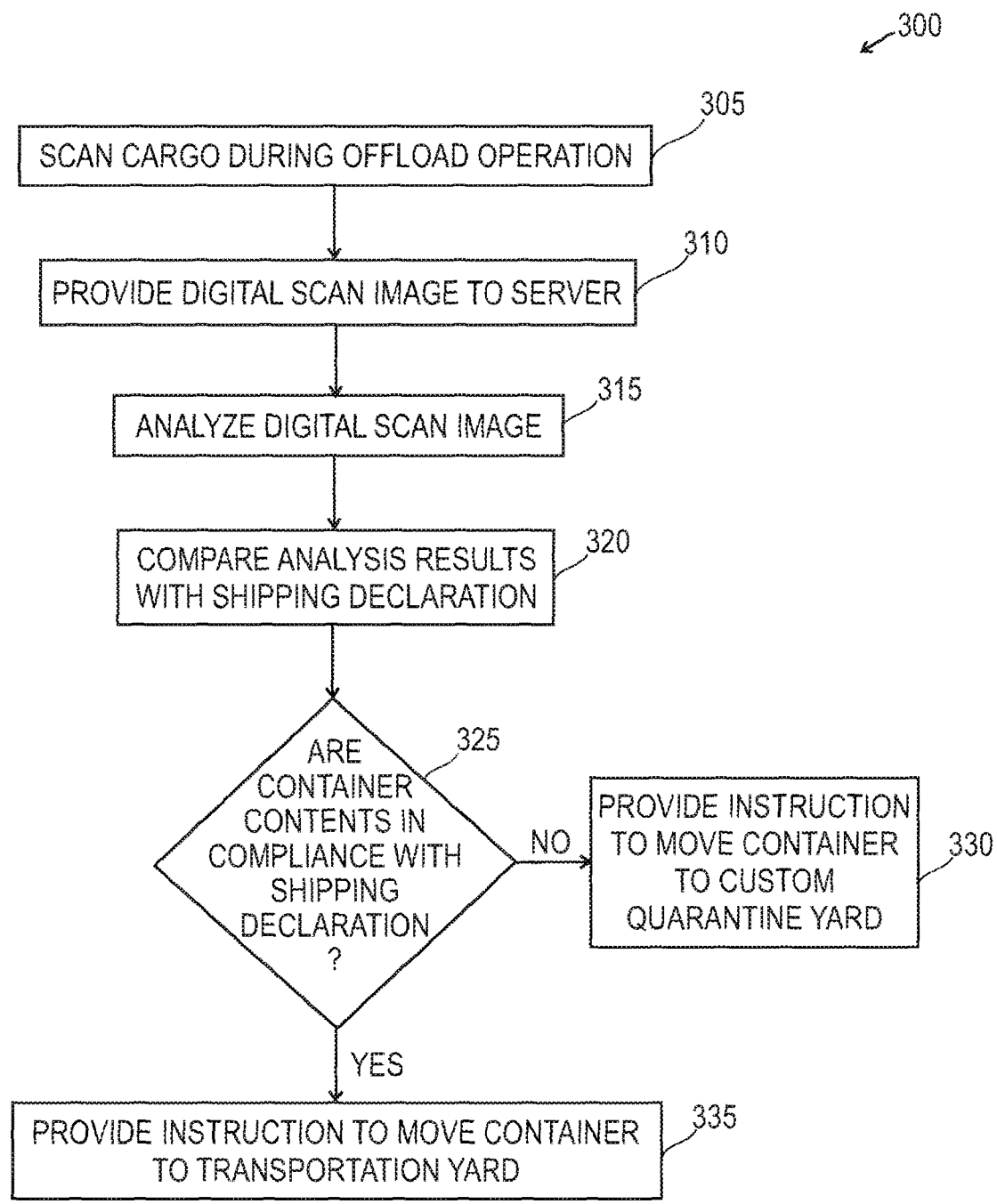
FIG. 3 depicts a flowchart of a process for inspecting cargo in accordance with embodiments.

FIG. 3 depicts a flowchart of cargo inspection process 300 in accordance with embodiments. For purposes of discussion, cargo inspection process 300 is described in operation with elements of system 100. Embodying methods are not so limited, and cargo inspection process 300 can operate with other systems having non-invasive image scanning system(s), server, electronic communication networks, and other components.

As a container is offloaded from a ship, non-invasive image scanning system 110A, 110B can obtain, step 305, a digital image of the cargo contents within the container. The digital scan image can be provided, step 310, to server (e.g. server 150, FIG. 1) through electronic communication network 140. In some implementations, the digital scan image can be stored in digital scan image records 126.

Computer vision system 154 can analyze, step 315, the images within the digital scan with images of expected cargo. This analysis can provide a list of the container contents based on the digital scan images. The expected cargo can be determined by accessing a cargo declaration within cargo declaration records 124, where the cargo declaration can be associated with the particular container. The cargo declaration can include cargo identifiers (e.g., stock keeping units (SKUs), or other identifiers). These cargo identifiers can be used by the computer vision system to locate cargo image patterns within cargo image pattern records 134. The cargo image patterns can be used by the computer vision system 154 to compare, step 320, the analysis results from step 315 to determine whether the container contents matches the content listing of the cargo declaration—for example, does the cargo listed on the cargo declaration match the container contents? does the content quantity match the declared content? is there any contraband within the container.

A determination is made, step 325, as to whether the container contents are in compliance with the cargo declaration. If the contents do not match the cargo declaration and/or contraband is detected, the cargo inspection system provides instruction to move the container to a customs quarantine yard, step 330. In the customs quarantine yard further inspection of the container can be performed.

If the contents do match the declaration and no contraband is detected, the cargo inspection system provides instruction to move the container to a transportation yard, step 335. From the transportation yard, the container can be released for entry into the country.

Figure 4:
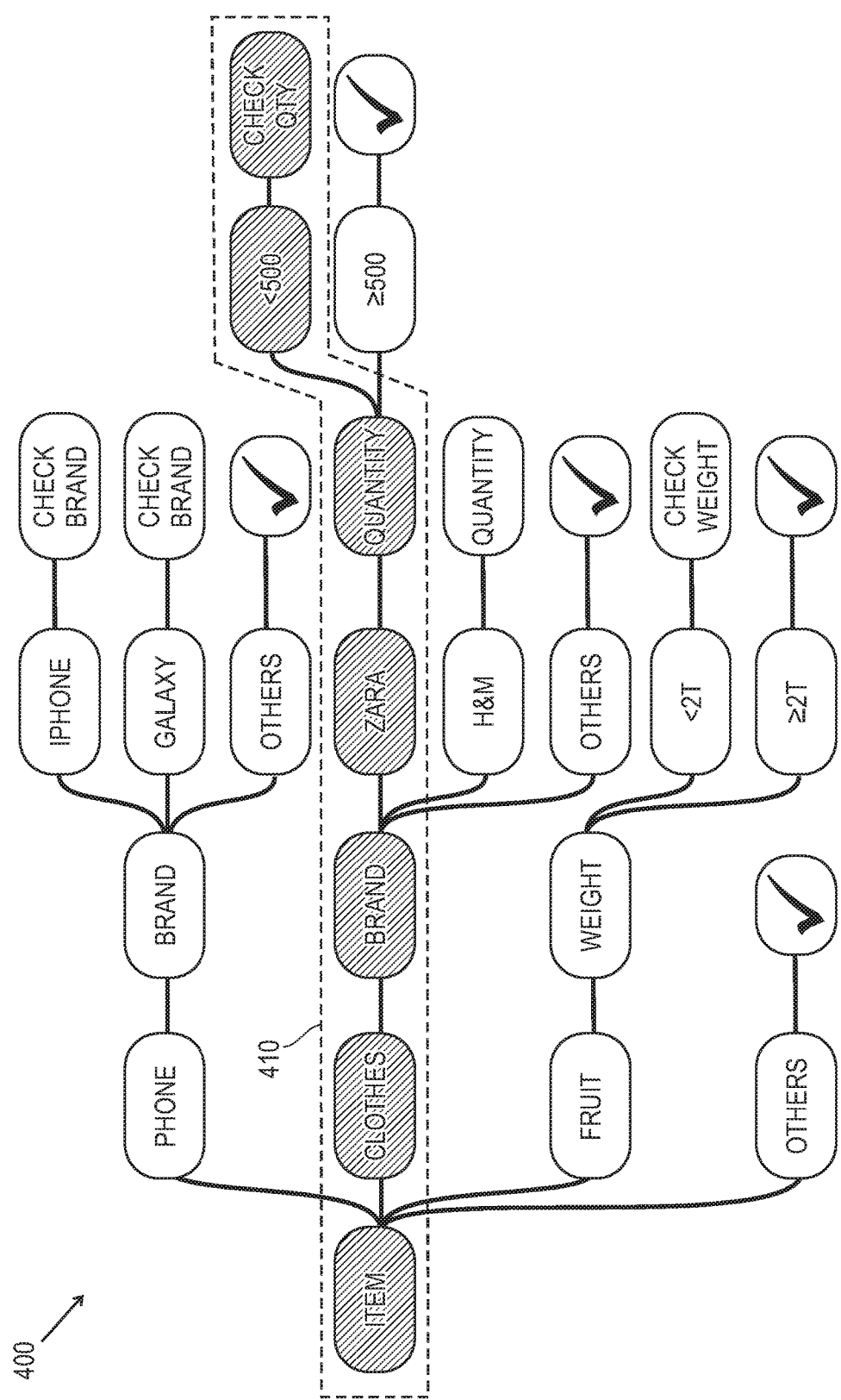
FIG. 4 depicts a decision tree used to train a computer vision system in accordance with embodiments.

FIG. 4 depicts training decision tree 400 used to train computer vision system, such as the computer vision system 154 from FIG. 1, in accordance with embodiments. Decision tree 400 can be used in conjunction with a non-parametric supervised learning method to train computer vision system 154 to perform classification and regression. The decision tree represents a branching method to illustrate every possible outcome of a decision. The computer vision system can apply a model to predict a value of a target variable by learning simple decision rules inferred from the data features of the decision tree.

The decision tree is built from historical custom inspection data. The decision tree is a predictive model that represents a mapping between object's attributes and the predicted result. Non-parametric model can be one feature of the decision tree. The difference between parametric models and non-parametric models is that the former has a fixed number of attributes, while the latter grows the number of attributes with the amount of training data. The attributes of decision tree are determined by the training data in the case of non-parametric statistics.

In accordance with embodiments, a decision tree can incorporate a vast amount of historical data provided by the national customs office experience. This historical data can be used as training data to build a decision tree. Each branch of decision tree 400 can represent items, brand, quantity, weight, etc. By way of example, highlighted path 410 indicates that a cargo declaration can declare that the container's contents include 500 piece goods of a known designer (Zara). The last bubble of highlighted path 410 includes a check sign. Because the quantity is less than 500 pieces, the decision tree suggests that a customs official manually inspect (i.e., check) the quantity of clothing.

The computer vision system can apply the decision tree in conjunction with the cargo declaration statements to ascertain the contents of the container, and whether there are any smuggled goods (e.g., undeclared and/or contraband cargo) in the container.

In accordance with embodiments, computer vision system 154 can implement an Iterative Dichotomiser 3 (ID3) algorithm in applying the decision tree. Implementations of the ID3 algorithm can create a multi-way tree, where each node includes a representation of a categorical feature that can yield the largest information gain for categorical targets. Trees are grown to their maximum size, and then a pruning step is usually applied to improve the ability of the tree to generalize to unseen data.

Sample data used by the ID3 can include:

Attribute-value description—attributes describe each example and have a fixed number of values;

Predefined classes—an example's attributes are defined, and provided to ID3;

Discrete classes—classes are sharply delineated, where continuous classes are segregated into categories. For example, a metal can be "hard," "quite hard, flexible," "soft," "quite soft" etc.

Sufficient examples—inductive generalization is used (i.e., not provable), therefore a sufficient number of cases is needed to distinguish valid patterns from chance occurrences.

The ID3 algorithm applies the statistical property of "information gain" in determining which attribute is best for the particular declared cargo. Gain measures how well a given attribute separates training examples into targeted classes. The attribute with the most useful classification is selected. Entropy measures the amount of information in an attribute.

The ID3 algorithm is a decision tree algorithm. In decision tree learning, a decision tree can be generated from a dataset. For example, Table I contains a data set representative of cargo identified in a cargo declaration.

TABLE I

| Declaration | Item | Brand | Quantity | Check |
|---|---|---|---|---|
| 1 | Clothes | ZARA | 600 | True |
| 2 | Phone | Iphone | — | True |
| 3 | Phone | Galaxy | — | True |
| 4 | Phone | Others | — | False |
| n | Clothes | H&M | . . . | . . . |

Given a collection S of outcomes:

$$\text{Entropy}(S) = \Sigma_{i=1}^{c} -p_i \log_2 p_i \qquad \text{EQ. 1}$$

Where: n=the sample data set (e.g. contains all items identified in a cargo declaration);

S=one kind of attribute in the sample data set (e.g., item, brand, quantity, etc.);

i=set of classes in S; and $p_i$=the proportion of the number of elements in class i to the number of elements in the whole data set.

In accordance with implementations of the ID3 algorithm, if every attribute of the decision tree is to be verified, then a new decision tree is generated to predict results. Else, Entropy(S) is calculated by applying Equation 1. The largest value of Entropy(S) is selected as a node of the decision tree. The set can be classified by attribute S, if not, the new decision tree is generated in units of S based on the attribute set.

Figure 5A:
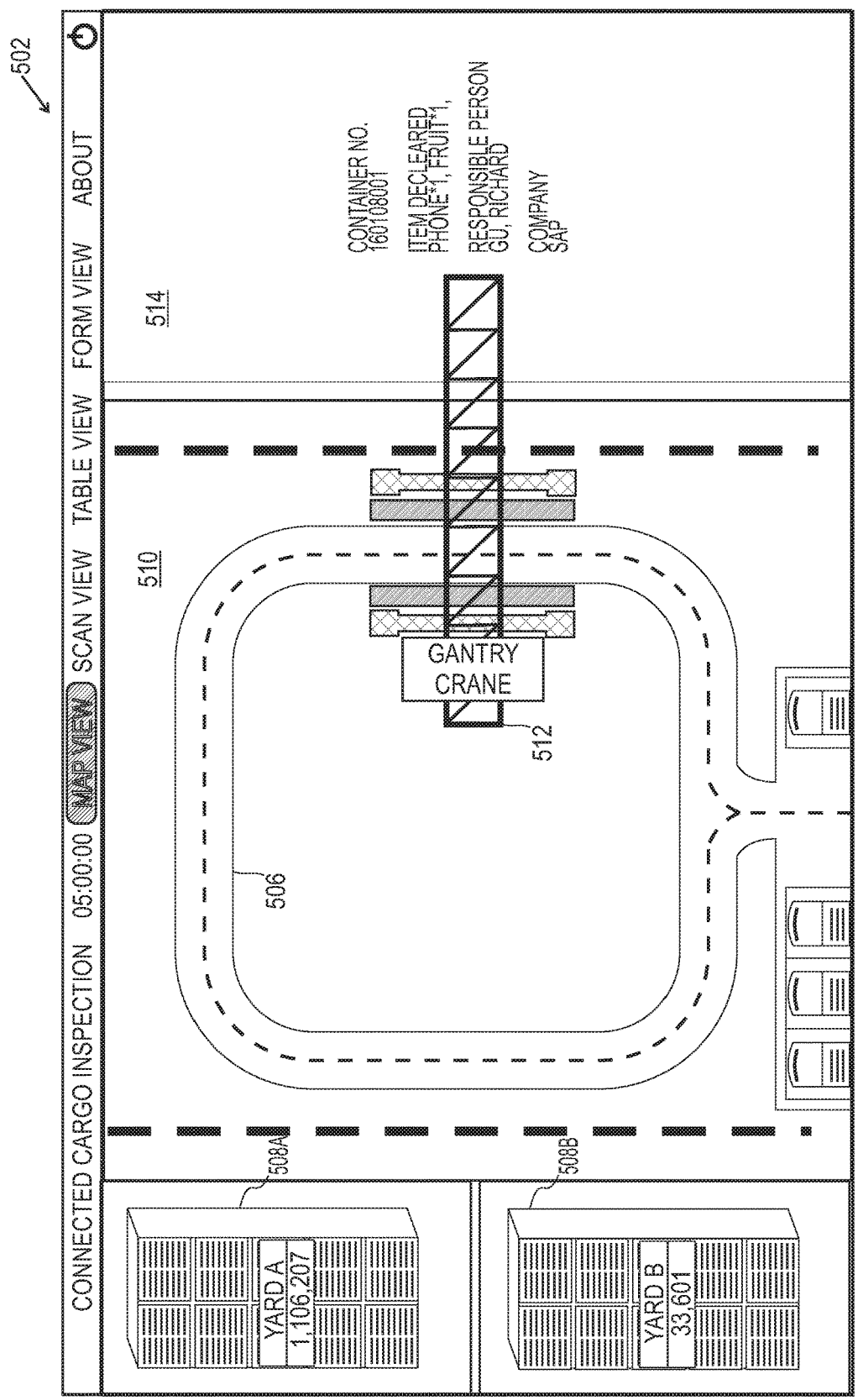

FIG. 5A depicts port plan graphical display 502 in accordance with embodiments. Port layout 510 depicts roadway 506, and includes locations of equipment (e.g., container location 508A, 508B, gantry crane 512, ship dockage, etc.). Activities occurring in the port can be displayed in about real time on port plan graphical display 502. Pane 514 includes information regarding contents of a cargo declaration. Other textual information can also be provided for display in pane 514.

Figure 5B:
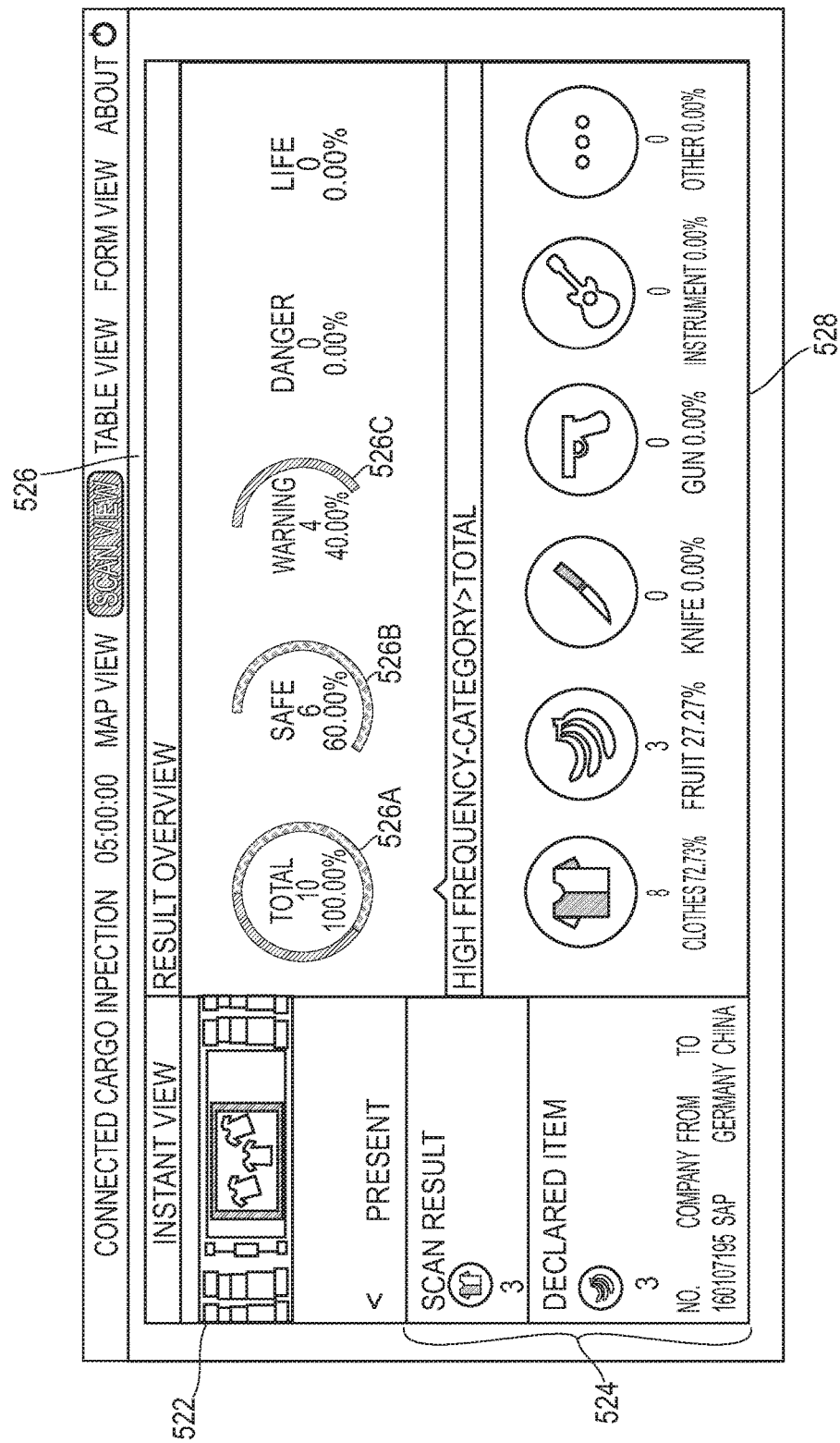

FIG. 5B depicts scan view graphical display 520 having four panes in accordance with embodiments. Container depiction pane 522 represents the digital scan image obtained from scanning the container. The contents of the container are depicted in situ. For purposes of illustration, the non-invasive image is replaced with a pictorial mock-up of the cargo contents. Contradistinction pane 524 provides information detailing any distinction(s) between items appearing in the cargo declaration and the contents detected as a result of computer vision system 154 analysis of the scan image. In the depicted example, the scan result block indicates three items of clothing. However, the declared item block indicates that the declaration lists three items of fruit. In the event of a contradistinction, an icon in the pane can alert a user to this status, for example, through use of colors.

Result overview pane 526 depicts ring charts containing data reports of various results obtained from analysis of the computer vision report. For example, ring chart 526A indicates there are 10 items identified in the cargo declaration. Ring chart 526B indicates that there are 6 safe item. Ring chart 526C indicates that 4 items have a warning status. In the illustrated example, none of the items were deemed to be dangerous nor were any live items detected in the container. One or more of the ring charts presented in results overview pane 526 can be dynamically selected by a user. Selection of a ring chart determines what is presented in item distribution pane 528.

Item distribution pane 528 depicts item icons representing the items identified by the computer vision system analysis. Item distribution pane 528 dynamically depicts icons representative of the identified contents. In the depicted example, the selected ring chart category is "TOTAL" (ring chart 526A). Associated with the content icons are the quantities of each item and its percentage of overall contents. As illustrated, there are 10 items in ring chart 526A, but a sum of item counts in pane 528 indicates there are 11 items. This discrepancy can be further investigated to determine if undeclared items are present in the container. In accordance with implementations, pane 528 can include contraband icons (e.g., knife, gun, etc.) even when no contraband items are detected to provide a quick visual assurance of no contraband being present in the container.

FIG. 5C depicts list form dialog graphical display 530. The list form can be generated by selection of an icon depicted in scan view graphical display 520, FIG. 5B. FIG. 5D depicts history log dialog graphical display 540 showing detail information of the list in tabular format.

In accordance with embodying systems and methods, object detection can be implemented based on the apparent feature vector of an object. This approach includes extracting a histogram of oriented gradient (HOG) features of item samples and detected objects, train features and detect objects with the computer vision system implemented, in one embodiment, as a support vector machine (SVM).

In accordance with embodiments, local object appearance and shape within an image can be described by the distribution of intensity gradients or edge directions when applying the HOG descriptor. The image is divided into small connected regions called cells, and for the pixels within each cell, a histogram of gradient directions is compiled. The HOG descriptor is the concatenation of these histograms. For improved accuracy, the local histograms can be contrast-normalized by calculating a measure of the intensity across a larger region of the image, called a block, and then using this value to normalize all cells within the block. This normalization results in better invariance to changes in illumination and shadowing. When described using a HOG descriptor, an image object's edge features and area size are less sensitive to illumination changes.

Extraction of a HOG descriptor for an image can be achieved by converting the image to grayscale, normalizing the color space with a Gamma correction method, calculating magnitude and direction gradients for each image pixel. The image can be divided into cells (e.g., a cell can be 8×8 pixels), the gradient histogram for each cell can be counted to get the cell HOG descriptor, blocks can be formed from the cells (e.g., 2×2 cells per block) and a block descriptor determined by connecting the cell HOG descriptor, the image HOG descriptor can then be obtained by connecting all the block descriptors.

A pixel's magnitude and direction gradient can be calculated based on the pixel value, a horizontal gradient of the pixel, and a vertical gradient of the pixel. In accordance with embodiments, to reduce any change in the magnitude gradient due to a possible change in image contrast over a local region, the gradient histogram can be normalized to the block HOG descriptor. This normalization can reduce the influence of local gradients.

SVM is a machine learning method that can be implemented by machine learning system 156 to heuristically improve the computer visions system analysis. SVM combines structure risk minimization with Vapnik-Chervonenkis (VC) dimension theory. This combination of techniques allows SVM to find a balance between complex simulations and learning even if a limited amount of samples is available. The input space is non-linearly transformed, and then mapped a high dimensional kernel space, to result in a lower VC dimension optimal hyperplane in high-dimensional kernel space.

The support vector machine method is based on the VC dimension theory and structural risk minimum principle of the statistical learning theory. Based on the limited sample, the SVM can obtain the best balance between the complexity of the model and learning. The SVM can address practical problems of machine learning such as small sample, nonlinearity, high dimension, and local minima. The SVM implements an inductive principle for model selection used for learning from finite training data sets. The model describes a general model of capacity control and provides a tradeoff between hypothesis space complexity (the VC dimension of approximating functions) and the quality of fitting the training data (empirical error).

In accordance with embodiments, an SVM can be implemented by first using a priori knowledge of the domain. Based on the domain, a class of functions can be chosen (e.g., polynomials of degree n, neural networks having n hidden layer neurons, a set of splines with n nodes, fuzzy logic models having n rules, etc.). The class of functions can be divided into a hierarchy of nested subsets in order of increasing complexity (e.g., polynomials of increasing degree). Empirical risk minimization can be performed on each subset (in essence, implementing parameter selection). A model whose sum of empirical risk and VC confidence is minimal is then selected from the series for use.

In accordance with some embodiments, a computer program application stored in non-volatile memory or computer-readable medium (e.g., register memory, processor cache, RAM, ROM, hard drive, flash memory, CD ROM, magnetic media, etc.) may include code or executable program instructions that when executed may instruct and/or cause a controller or processor to perform methods discussed herein such as a method for integrated cargo inspection utilizing non-invasive scanning equipment integrated into existing port facilities used during container offload operations from a cargo ship, as described above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

We claim:

1. A system for integrated cargo inspection, the system comprising:
    a non-invasive imaging system configured to scan a cargo container during an offload operation to obtain a digital scan image of contents within the cargo container;
    a server in communication with a data store across an electronic communication network, the server including a control processor configured to access executable program instructions to cause the control processor to control components of the system, including:
    a computer vision system configured to access the digital scan image, and to perform vision system recognition techniques on the digital scan image;
        the computer vision system configured to prepare an electronic computer vision report that includes one or more image icons representing the cargo container contents;
        a respective image icon of the one or more image icons depicting a drawing of a respective identified individual item of the identified individual items;
    the computer vision system configured to compare contents of the computer vision report with images of expected cargo and to determine whether the container contents match the expected cargo;
        a machine learning system configured to analytically review the computer vision report to provide heuristically generated analysis used to train the computer vision system; and
    a computing device in bidirectional communication with the server, the computing device including a display.

2. The system of claim 1, including the non-invasive imaging system in communication with the data store and configured to provide the digital scan image to a record repository in the data store.

3. The system of claim 1, including the non-invasive imaging system located on a gantry crane to move the cargo container during the offload operation.

4. The system of claim 1, including the computer vision system configured to access an electronic cargo declaration located in the data store, the electronic cargo declaration providing cargo identifiers for the cargo container contents.

5. The system of claim 1, including the machine learning system configured to implement a support vector machine learning method in combination with structure risk minimization.

6. The system of claim 1, including the port plan graphical display including a plan view of a port facility that displays about real time port activities occurring in the port.

7. The system of claim 1, including the scan view graphical display including:
    a container depiction pane represents contents of the cargo container identified from the digital scan image;
    a contradistinction pane providing information detailing distinctions between items listed on the cargo declaration and contents detected by the computer vision system in the digital scan image;
    a results overview pane depicting charts containing data reports obtained from analysis of the computer vision report; and
    an item distribution pane depicting one or more icons representing the identified contents of the cargo container, and a detected quantity of the identified contents.

8. The system of claim 1, including the results list form dialog generated by selection of an icon depicted in the scan view graphical display.

9. The system of claim 8, including the results history log including detail information of the list form dialog in tabular format.

10. A method for integrated cargo inspection, the method comprising:
    receiving a non-invasive imaging system digital scan image of contents within a cargo container;
    a computer vision system identifying individual items depicted in the digital scan image;
    accessing a cargo declaration to determine expected cargo contents of the cargo container;
    the computer vision system comparing the identified individual items with the expected cargo to determine the presence of contraband cargo;
    the computer vision system configured to prepare an electronic computer vision report that includes one or more image icons;
    a respective image icon of the one or more image icons depicting at least an outline drawing of a respective identified individual item of the identified individual items;
    if contraband cargo is present, providing instructions to move the cargo container to a quarantine yard; and
    if contraband cargo is not present, providing instructions to move the cargo container to a transportation yard.

11. The method of claim 10, including obtaining the digital scan image during an offload operation of the cargo container.

12. The method of claim 10, including the identifying including comparing the individual item depictions to cargo image pattern records.

13. The method of claim 10, including locating cargo image patterns in a data store based on cargo identifiers in the cargo declaration.

14. The method of claim 10, the computer vision system analyzing images of the identified individual items from the digital image scan with cargo image patterns located in a data store.

15. The method of claim 14, including a machine learning system analytically reviewing the computer vision report to provide heuristically generated analysis to train the computer vision system.

16. A non-transitory computer-readable medium having stored thereon instructions which when executed by a control processor cause the control processor to perform a method for integrated cargo inspection, the method comprising:
    receiving a non-invasive imaging system digital scan image of contents within a cargo container;
    identifying individual items depicted in the digital scan image;
    accessing a cargo declaration to determine expected cargo contents of the cargo container;
    comparing the identified individual items with the expected cargo to determine the presence of contraband cargo;
    preparing an electronic computer vision report that includes one or more image icons;

a respective image icon of the one or more image icons depicting at least an outline drawing of a respective identified individual item of the identified individual items;

if contraband cargo is present, providing instructions to move the cargo container to a quarantine yard; and if contraband cargo is not present, providing instructions to move the cargo container to a transportation yard.

17. The non-transitory computer-readable medium of claim 16, the instructions further configured to cause the control processor to perform the steps of:

comparing the individual item depictions to cargo image pattern records;

locating cargo image patterns in a data store based on cargo identifiers in the cargo declaration; and a computer vision system analyzing images of the identified individual items from the digital image scan with the cargo image patterns.

18. The non-transitory computer-readable medium of claim 17, the instructions further configured to cause the control processor to perform the steps of:

comparing the individual item depictions to cargo image pattern records;

locating cargo image patterns in a data store based on cargo identifiers in the cargo declaration; and a computer vision system analyzing images of the identified individual items from the digital image scan with the cargo image patterns.

19. The non-transitory computer-readable medium of claim 18, the instructions further configured to cause the control processor to perform the step of a machine learning system analytically reviewing the computer vision report to provide heuristically generated analysis to train the computer vision system.

* * * * *